United States Patent
Fuerst et al.

(10) Patent No.: US 12,144,690 B2
(45) Date of Patent: Nov. 19, 2024

(54) THREE DIMENSIONAL MEDICAL IMAGING AND INTERACTIONS

(71) Applicant: Verb Surgical Inc., Santa Clara, CA (US)

(72) Inventors: Bernhard A. Fuerst, Sunnyvale, CA (US); Alexander Barthel, Santa Clara, CA (US); Eric M. Johnson, Half Moon Bay, CA (US); Risto Kojcev, Cupertino, CA (US)

(73) Assignee: Verb Surgical Inc., Santa Clara, CA (US)

( * ) Notice: Subject to any disclaimer, the term of this patent is extended or adjusted under 35 U.S.C. 154(b) by 787 days.

(21) Appl. No.: 17/162,565

(22) Filed: Jan. 29, 2021

(65) Prior Publication Data

US 2021/0236233 A1    Aug. 5, 2021

Related U.S. Application Data

(60) Provisional application No. 62/967,810, filed on Jan. 30, 2020.

(51) Int. Cl.
*A61B 34/30* (2016.01)
*A61B 1/00* (2006.01)
(Continued)

(52) U.S. Cl.
CPC ...... *A61B 90/361* (2016.02); *A61B 1/000095* (2022.02); *A61B 34/25* (2016.02); *A61B 34/37* (2016.02); *A61B 34/74* (2016.02); *A61B 90/37* (2016.02); *G06F 3/04845* (2013.01); *G06F 3/0485* (2013.01); *G16H 20/40* (2018.01); *G16H 30/40* (2018.01); *G16H 40/67* (2018.01); *H04N 13/156* (2018.05); *H04N 13/302* (2018.05); *H04N 13/383* (2018.05);
(Continued)

(58) Field of Classification Search
CPC . A61B 19/201; A61B 19/203; A61B 19/5244; A61B 34/00; A61B 34/30; A61B 34/40; A61B 34/37; A61B 90/00; A61B 90/37; A61B 34/74
See application file for complete search history.

(56) References Cited

U.S. PATENT DOCUMENTS 10,895,757 B2    1/2021  Fuerst et al.
2013/0242053 A1*  9/2013  Bjelkhagen .......... H04N 13/302
                                                    348/45

(Continued)

FOREIGN PATENT DOCUMENTS

WO       2020009731       1/2020

OTHER PUBLICATIONS

Invitational to Pay Additional Fees and Partial Search Report for International Application No. PCT/US2021/015905 mailed Apr. 19, 2021, 12 pages.

(Continued)

*Primary Examiner* — Vi X Nguyen
(74) *Attorney, Agent, or Firm* — Aikin & Gallant, LLP

(57) ABSTRACT

A medical image viewer can render to a display, a three-dimensional view of patient anatomy, a multi planar reconstruction (MPR) view of the patient anatomy, and an intra-operational view. Some of the views can be synchronized to show a common focal point of the anatomy. Other embodiments are described and claimed.

22 Claims, 11 Drawing Sheets

(51) Int. Cl.

| | |
|---|---|
| *A61B 34/00* | (2016.01) |
| *A61B 34/37* | (2016.01) |
| *A61B 90/00* | (2016.01) |
| *G06F 3/04845* | (2022.01) |
| *G06F 3/0485* | (2022.01) |
| *G16H 20/40* | (2018.01) |
| *G16H 30/40* | (2018.01) |
| *G16H 40/67* | (2018.01) |
| *H04N 13/156* | (2018.01) |
| *H04N 13/302* | (2018.01) |
| *H04N 13/383* | (2018.01) |
| *H04N 13/398* | (2018.01) |
| *A61B 5/06* | (2006.01) |
| *G06F 3/0482* | (2013.01) |
| *G06F 3/0488* | (2022.01) |

(52) U.S. Cl.
CPC ............ *H04N 13/398* (2018.05); *A61B 5/066* (2013.01); *A61B 2090/3612* (2016.02); *A61B 2090/365* (2016.02); *A61B 2090/367* (2016.02); *A61B 2090/372* (2016.02); *A61B 2090/373* (2016.02); *A61B 2090/374* (2016.02); *A61B 2090/3762* (2016.02); *A61B 2090/378* (2016.02); *G06F 3/0482* (2013.01); *G06F 3/0488* (2013.01); *H04N 2213/008* (2013.01)

(56) References Cited

U.S. PATENT DOCUMENTS

2019/0298481 A1* 10/2019 Rosenberg ............ A61B 90/00
2019/0380791 A1    12/2019 Fuerst et al.

OTHER PUBLICATIONS

Oguma, Ryo, et al., "Ultrasound Image Overlay onto Endoscopic Image by Fusing 2D-3D Tracking of Laparoscopic Ultrasound Probe," Workshop on Augmented Environments for Computer-Assisted Interventions, Sep. 2014, pp. 14-22.

Khan, Martin, et al., "Overlay visualization in endoscopic ENT surgery," International Journal of Computer Assisted Radiology and Surgery, Jun. 2011, 7 pages.

International Preliminary Report on Patentability for International Application No. PCT/US2021/015905 maied Aug. 11, 2022, 11 pages.

International Search Report and Written Opinion for International Application No. PCT/US2021/015905 mailed Jun. 10, 2021, 18 pages.

* cited by examiner

THREE DIMENSIONAL MEDICAL IMAGING AND INTERACTIONS

CROSS-REFERENCE TO RELATED APPLICATIONS

This application claims benefit of U.S. provisional application No. 62/967,810 filed Jan. 30, 2020.

TECHNICAL FIELD

This disclosure relates generally to the field of surgical robotics and, more particularly, to displaying and interacting with three dimensional imagery of a patient with a surgical robotic system.

BACKGROUND

Minimally-invasive surgery (MIS), such as laparoscopic surgery, involves techniques intended to reduce tissue damage during a surgical procedure. For example, laparoscopic procedures typically involve creating a number of small incisions in the patient (e.g., in the abdomen), and introducing one or more tools and at least one endoscopic camera through the incisions into the patient. The surgical procedures are then performed by using the introduced tools, with the visualization aid provided by the camera.

Generally, MIS provides multiple benefits, such as reduced patient scarring, less patient pain, shorter patient recovery periods, and lower medical treatment costs associated with patient recovery. In some embodiments, MIS may be performed with surgical robotic systems that include one or more robotic arms for manipulating surgical instruments based on commands from an operator. For example, an operator may provide commands for manipulating surgical instruments, while viewing an image that is provided by a camera and displayed on a display to the user. Conventional display systems fall short, however, in enabling effective control of the display systems or of surgical robotic systems. Furthermore, conventional display systems generally provide two-dimensional surgical image data to the user, and current three dimensional displays typically require the user to wear glasses or additional, similar wearable components (e.g., with polarizing filters or dynamic shutters) for visualization of three-dimensional images. Such glasses and additional wearable components, however, may be problematic to use and handle in surgical or sterile environments. During a surgical procedure with a surgical robotic system, a surgeon may wish to view image data of the patient that can help the surgeon navigate anatomy of the patient. Thus, there is a need for improved three dimensional display systems that enables a user to better visualize the surgical site during a surgical procedure performed with a surgical robotic system.

SUMMARY

Generally, a surgical robotic system with an interactive three dimensional display can include a left handheld user interface device (UID) and right handheld UID, and an autostereoscopic three dimensional display. One or more computer processors of the surgical robotic system can be configured to receive a plurality of pre-operation images of a patient and perform reconstruction upon the pre-operation images to generate a three dimensional image of the patient. The processor can render the three dimensional image of the patient stereoscopically, resulting in a stereoscopic data stream having a first set of data representing a left eye position and a second set of data representing a right eye position. The autostereoscopic three dimensional display can be driven with the stereoscopic data stream to produce one or more views of the three dimensional image of the patient on the autostereoscopic three dimensional display. The processor can adjust a view of the three dimensional image of the patient on the autostereoscopic three dimensional display in response to an input from the left and/or right UIDs. The same UIDs can be used to control surgical robotic arms (and/or attached tools) to perform the surgical procedure, thus allowing a user to seamlessly toggle between viewing a three-dimensional image of the patient and performing surgery upon the patient.

In some embodiments, an endoscopic view of the patient and the surgical worksite shown on the three dimensional display simultaneously with the three dimensional image of the patient. The user can gain an improved understanding of the patient's anatomy which can navigation of surgical tools to affect the surgical procedure.

DETAILED DESCRIPTION

Non-limiting examples of various aspects and variations of the invention are described herein and illustrated in the accompanying drawings.

Figure 1:
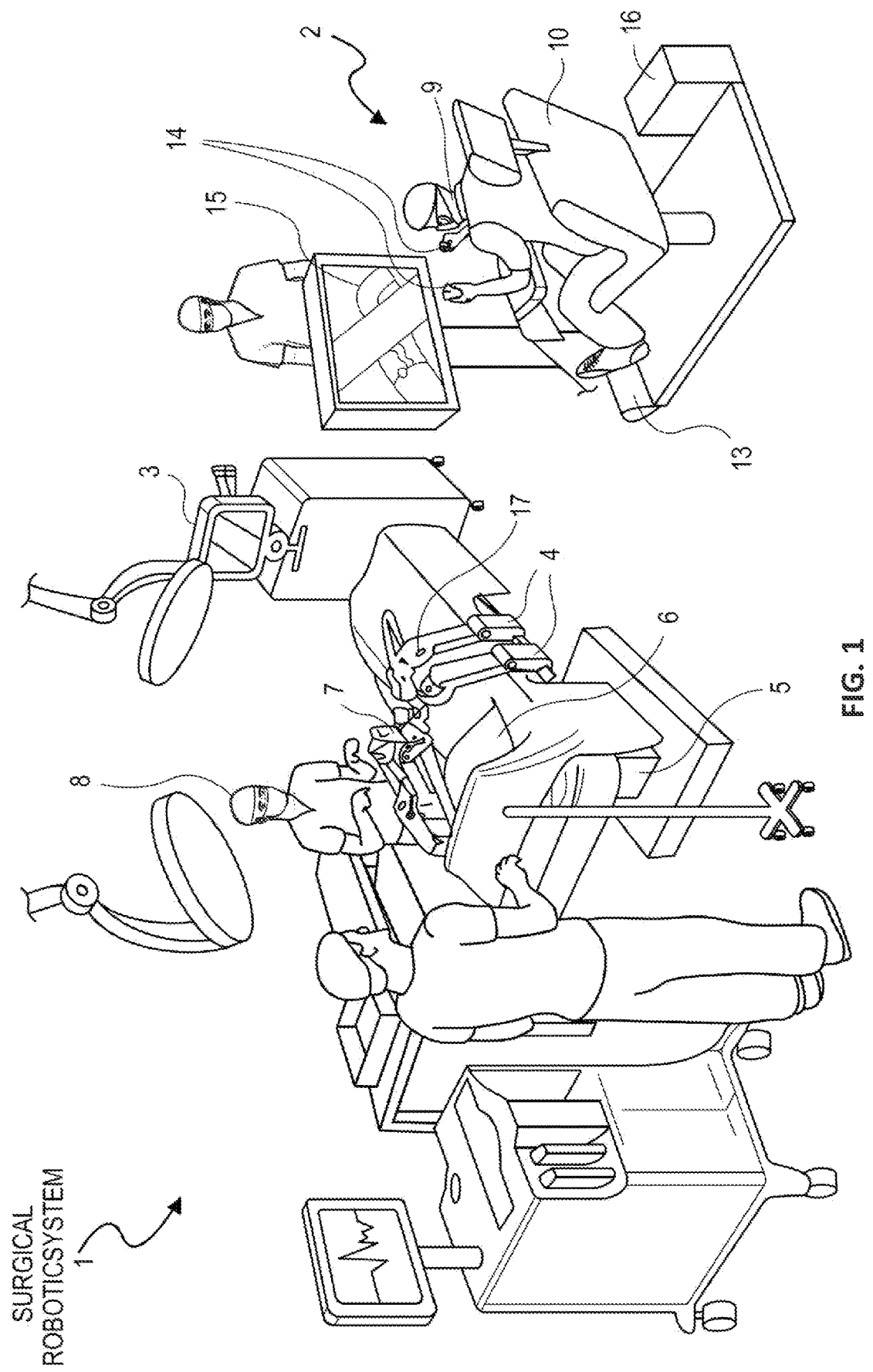
FIG. 1 is a pictorial view of an example surgical robotic system in an operating arena, according to some embodiments.

Referring to FIG. 1, this is a pictorial view of an example surgical robotic system 1 in an operating arena. The robotic system 1 includes a user console 2, a control tower 3, and one or more surgical robotic arms 4 at a surgical robotic platform 5, e.g., a table, a bed, etc. The system 1 can incorporate any number of devices, tools, or accessories used to perform surgery on a patient 6. For example, the system 1 may include one or more surgical tools 7 used to perform surgery. A surgical tool 7 may be an end effector that is attached to a distal end of a surgical arm 4, for executing a surgical procedure. In one aspect, the arms 4 may be mounted to a table or bed on which the patient rests as shown in the example of FIG. 1, or they may be mounted to a cart separate from the table or bed.

Each surgical tool 7 may be manipulated manually, robotically, or both, during the surgery. For example, the surgical tool 7 may be a tool used to enter, view, or manipulate an internal anatomy of the patient 6. In one embodiment, the surgical tool 7 is a grasper that can grasp tissue of the patient. The surgical tool 7 may be controlled manually, by a bedside operator 8; or it may be controlled robotically, via actuated movement of the surgical robotic arm 4 to which it is attached. The robotic arms 4 are shown as a table-mounted system, but in other configurations the arms 4 may be mounted in a cart, ceiling or sidewall, or in another suitable structural support.

Generally, a remote operator 9, such as a surgeon or other operator, may use the user console 2 to remotely manipulate the arms 4 or the attached surgical tools 7, e.g., teleoperation. The user console 2 may be located in the same operating room as the rest of the system 1, as shown in FIG. 1. In other environments, however, the user console 2 may be located in an adjacent or nearby room, or it may be at a remote location, e.g., in a different building, city, or country. The user console 2 may comprise a seat 10, foot-operated controls 13, one or more handheld user input devices, UID 14, and at least one user display 15 that is configured to display, for example, a view of the surgical site inside the patient 6. In the example user console 2, the remote operator 9 is sitting in the seat 10 and viewing the user display 15 while manipulating a foot-operated control 13 and a handheld UID 14 in order to remotely control the arms 4 and the surgical tools 7 (that are mounted on the distal ends of the arms 4.)

In some variations, the bedside operator 8 may also operate the system 1 in an "over the bed" mode, in which the beside operator 8 (user) is now at a side of the patient 6 and is simultaneously manipulating a robotically-driven tool (end effector as attached to the arm 4), e.g., with a handheld UID 14 held in one hand, and a manual laparoscopic tool. For example, the bedside operator's left hand may be manipulating the handheld UID to control a robotic component, while the bedside operator's right hand may be manipulating a manual laparoscopic tool. Thus, in these variations, the bedside operator 8 may perform both robotic-assisted minimally invasive surgery and manual laparoscopic surgery on the patient 6.

During an example procedure (surgery), the patient 6 is prepped and draped in a sterile fashion to achieve anesthesia. Initial access to the surgical site may be performed manually while the arms of the robotic system 1 are in a stowed configuration or withdrawn configuration (to facilitate access to the surgical site.) Once access is completed, initial positioning or preparation of the robotic system 1 including its arms 4 may be performed. Next, the surgery proceeds with the remote operator 9 at the user console 2 utilizing the foot-operated controls 13 and the UIDs 14 to manipulate the various end effectors and perhaps an imaging system, to perform the surgery. Manual assistance may also be provided at the procedure bed or table, by sterile-gowned bedside personnel, e.g., the bedside operator 8 who may perform tasks such as retracting tissues, performing manual repositioning, and tool exchange upon one or more of the robotic arms 4. Non-sterile personnel may also be present to assist the remote operator 9 at the user console 2. When the procedure or surgery is completed, the system 1 and the user console 2 may be configured or set in a state to facilitate post-operative procedures such as cleaning or sterilization and healthcare record entry or printout via the user console 2.

In one embodiment, the remote operator 9 holds and moves the UID 14 to provide an input command to move a robot arm actuator 17 in the robotic system 1. The UID 14 may be communicatively coupled to the rest of the robotic system 1, e.g., via a console computer system 16. The UID 14 can generate spatial state signals corresponding to movement of the UID 14, e.g. position and orientation of the handheld housing of the UID, and the spatial state signals may be input signals to control a motion of the robot arm actuator 17. The robotic system 1 may use control signals derived from the spatial state signals, to control proportional motion of the actuator 17. In one embodiment, a console processor of the console computer system 16 receives the spatial state signals and generates the corresponding control signals. Based on these control signals, which control how the actuator 17 is energized to move a segment or link of the arm 4, the movement of a corresponding surgical tool that is attached to the arm may mimic the movement of the UID 14. Similarly, interaction between the remote operator 9 and the UID 14 can generate for example a grip control signal that causes a jaw of a grasper of the surgical tool 7 to close and grip the tissue of patient 6.

The surgical robotic system 1 may include several UIDs 14, where respective control signals are generated for each UID that control the actuators and the surgical tool (end effector) of a respective arm 4. For example, the remote operator 9 may move a first UID 14 to control the motion of an actuator 17 that is in a left robotic arm, where the actuator responds by moving linkages, gears, etc., in that arm 4. Similarly, movement of a second UID 14 by the remote operator 9 controls the motion of another actuator 17, which in turn moves other linkages, gears, etc., of the robotic system 1. The robotic system 1 may include a right arm 4 that is secured to the bed or table to the right side of the patient, and a left arm 4 that is at the left side of the patient. An actuator 17 may include one or more motors that are controlled so that they drive the rotation of a joint of the arm 4, to for example change, relative to the patient, an orientation of an endoscope or a grasper of the surgical tool 7 that is attached to that arm. Motion of several actuators 17 in the same arm 4 can be controlled by the spatial state signals generated from a particular UID 14. The UIDs 14 can also control motion of respective surgical tool graspers. For example, each UID 14 can generate a respective grip signal to control motion of an actuator, e.g., a linear actuator, that opens or closes jaws of the grasper at a distal end of surgical tool 7 to grip tissue within patient 6.

In some aspects, the communication between the platform 5 and the user console 2 may be through a control tower 3, which may translate user commands that are received from the user console 2 (and more particularly from the console computer system 16) into robotic control commands that transmitted to the arms 4 on the robotic platform 5. The control tower 3 may also transmit status and feedback from the platform 5 back to the user console 2. The communication connections between the robotic platform 5, the user console 2, and the control tower 3 may be via wired or wireless links, using any suitable ones of a variety of data communication protocols. Any wired connections may be optionally built into the floor or walls or ceiling of the operating room. The robotic system 1 may provide video output to one or more displays, including displays within the operating room as well as remote displays that are accessible via the Internet or other networks (e.g., the robotic system 1 can include one or more endoscopic cameras that provide video output or other suitable image data to the displays). The video output or feed may also be encrypted to ensure privacy and all or portions of the video output may be saved to a server or electronic healthcare record system.

Figure 2:
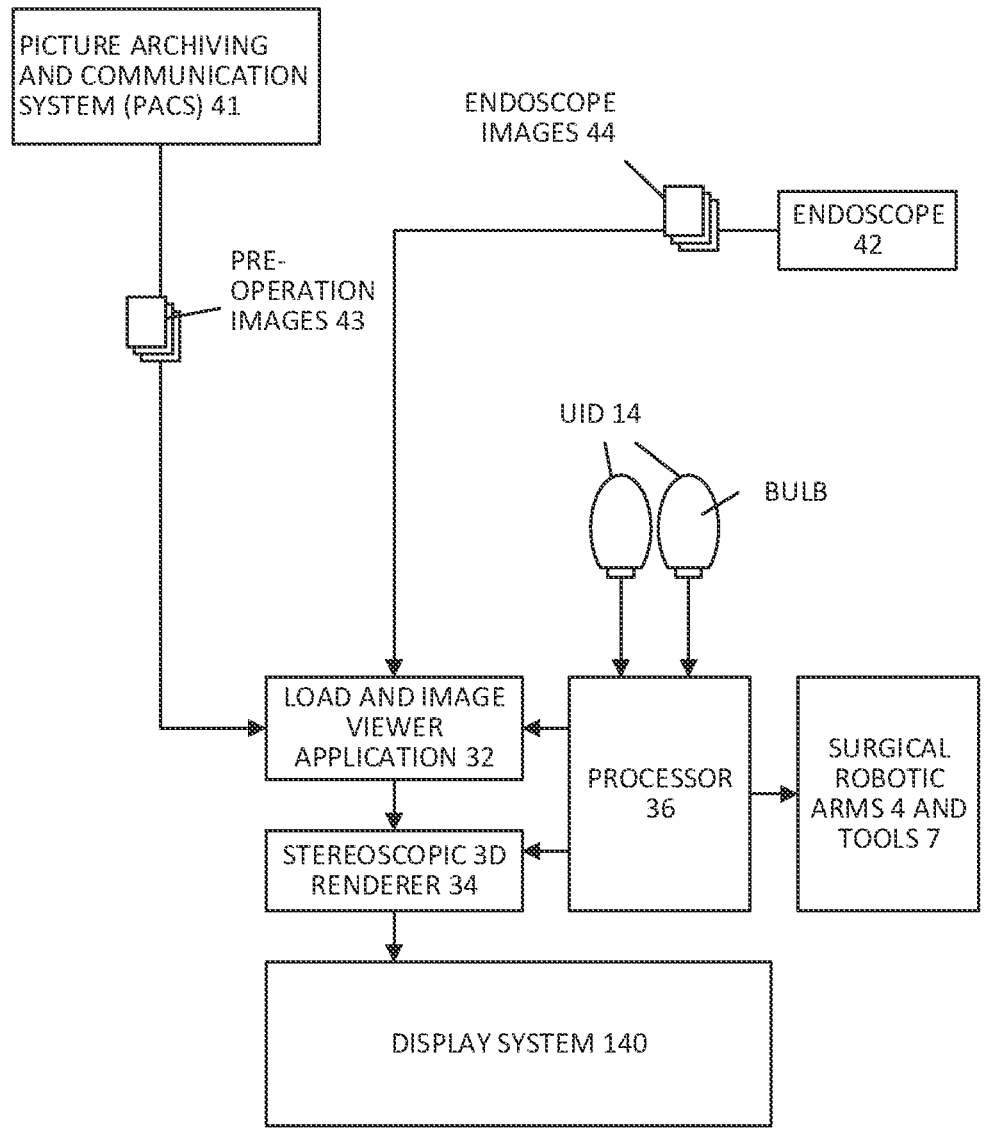
FIG. 2 shows a system diagram of a surgical robotic system with three dimensional viewing, according to some embodiments.

Referring to FIG. 2, a surgical robotic system 1 according to some embodiments is shown having features that allow a user (e.g., a surgeon) to browse pre-operation images of a patient in three-dimensional viewing space, during a procedure. This can provide a surgeon with additional information about the patient's anatomy that can help the surgeon properly navigate and perform the surgery on the patient with the surgical robotic system. The same UIDs and display used for performing the procedure can be used to present the three-dimensional pre-operation images, thereby allowing a surgeon to seamlessly view the pre-operation images while performing the surgery.

The surgical robotic system 1 includes a plurality of UIDs 14, e.g., a left handheld UID and right handheld UID. In some embodiments, each of UIDs has a bulb shaped portion that is activated upon being squeezed, and de-activated upon release. Additionally, or alternatively, the UIDs can have one or more buttons that are activated upon being pressed and de-activated when released. One or more processors 36 are configured to monitor an activation state of each UID (e.g., activated or deactivated). In some embodiments, each UID can have multiple inputs (e.g., a combination of buttons and/or a squeezable bulb), each input having an activation state that is monitored by the processor. The processor can track the position and movement of the UIDs as discussed in other sections.

The system can seamlessly provide access to three-dimensional viewing of pre-operation images during surgery, using the same hardware that is used for performing the surgery. For example, the processor is configured to control movement of a plurality of surgical robotic arms 4 and/or tools 7, in response to input from the left and/or right UIDs, to perform surgery upon the patient. The user can control the surgical arms on sight or remotely. A display system 140 can be an autostereoscopic three-dimensional display, used to view live images from the operation of the surgery (e.g., endoscope images 44 from an endoscope 42). The autostereoscopic three dimensional display can simultaneously produce a) the three dimensional view of the patient, and b) an endoscope view based on images received from an endoscope. The three dimensional display can be integrated with the user console such that the same display that is used to view the three dimensional image of the patient is also used to view the surgical worksite in the patient to coordinate movement of surgical tools in the surgical worksite. By seeing both views simultaneously, the user can gain a better understanding of the patient's anatomy and how to move the tools to perform the surgery.

Pre-operation images 43 can be received by a loader and image viewer application 32 from a picture archiving and communication system (PACS) 41. The PACS is a system for storing and accessing medical images from different modalities (e.g., computer tomography (CT) or Magnetic Resonance Imaging (MRI)) that are typically present in hospitals and other medical settings. The loader and viewer 32 is an application running on a surgical robotics system. Before a surgical procedure, the system receives the pre-operation images of the patient from the PACS. Those images can be stored as multi-frame Digital Imaging and Communications in Medicine (DICOM) files. DICOM is a standard that defines how medical images and their metadata are stored and exchanged.

The system (e.g., at loader and viewer application 32) can perform reconstruction on the plurality of pre-operation images 43 to generate a three dimensional image of the patient. The images, which can be stored as DICOM files, can each represent a "slice" of the patient. The slices can be combined to reconstruct a three-dimensional model of the patient, with one or more known techniques that can be performed by a processor. The pre-operation 2D images and the reconstructed three dimensional image can be represented by assigning intensities to each pixel (2D) or voxel (3D). The system can perform partitioning, thereby assigning a class to each pixel or voxel of those images, in structures or regions of interest (ROI) to yield a segmentation. Such segmentations can be obtained by manual, semi-automatic, or automatic annotation. Three dimensional visualizations, in particular segmentations, are useful to make structures transparent, such as those structures which are currently not of interest. In some embodiments, UID inputs can select segmentations of the three dimensional image of the patient, and command those segmentations to become transparent, so that a user can better see regions of interest (e.g., organs or tumors).

Additionally, medical image modalities, e.g. Computer Tomography (CT) or Magnetic Resonance Imaging (MRI), can require a reconstruction step before one can view the acquired data in image space. One way of presenting this data to the user after this reconstruction step is showing three slices or planes, sagittal, coronal, and transversal (also known as 'axial). Multi planar reconstruction (MPR) can be performed on the pre-operation images to generate a sagittal view, a coronal view, and transversal view of the patient. MPR involves converting data from an imaging modality acquired in a particular plane, typically axial (transversal), to one or more other planes. MPR can be performed using thin-slice data from volumetric CT-scanning in the axial plane, although other medical image modalities, such as MRI, and other planes can be used. The medical thin-slice images, for example from the axial plane, can then be converted to non-axial planes such as coronal, sagittal or oblique.

A stereoscopic three dimensional renderer 34 renders the three dimensional image of the patient stereoscopically, resulting in a stereoscopic data stream having a first set of data representing a left eye position and a second set of data representing a right eye position. Each set of data (e.g., a data stream) represents what each eye of a user sees on the three dimensional display. In one aspect, the renderer generates two virtual cameras, one for each data stream. The virtual cameras are positioned in virtual space such that they have a horizontal offset. In one embodiment, off-axis rendering is used to render the three dimensional image stereoscopically. In such a case, each virtual camera has a non-symmetric camera frustum. The view frustum is the region of space in the modeled 3D environment that may appear on the screen. In other words, it is the field of view of the virtual camera. Non-symmetric camera frustums can avoid viewing stress of the user. The two virtual cameras are placed in the same scene and share a single OpenGL context. Each virtual camera renders the respective data streams to separate viewports. In contrast, a "toe-in" technique simply points each virtual camera at the same focal point (without non-symmetric camera frustums), thereby introducing a vertical parallax that creates viewing stress in a user.

The display system 140, which can be an autostereoscopic three dimensional display, is driven with the stereoscopic data stream to produce one or more views of the three dimensional image of the patient on the display. A user can adjust a view of the three dimensional image of the patient on the autostereoscopic three dimensional display in response to an input from the left and/or right UIDs 14. It should be understood that the one or more processors 36 performs computer instructions (e.g., stored in non-volatile memory) to run applications such as load and image viewer application 32, stereoscopic 3D renderer 34, and other applications. Further, different processors can be dedicated to different tasks, for example, one can be dedicated to load and view images. Another can be dedicated to stereoscopic rendering. Another can be dedicated to monitoring UID activation states. Architecture relating to allocation of processing resources is not germane to the present disclosure and such architecture can vary without exceeding the scope of the present disclosure.

Figure 3:
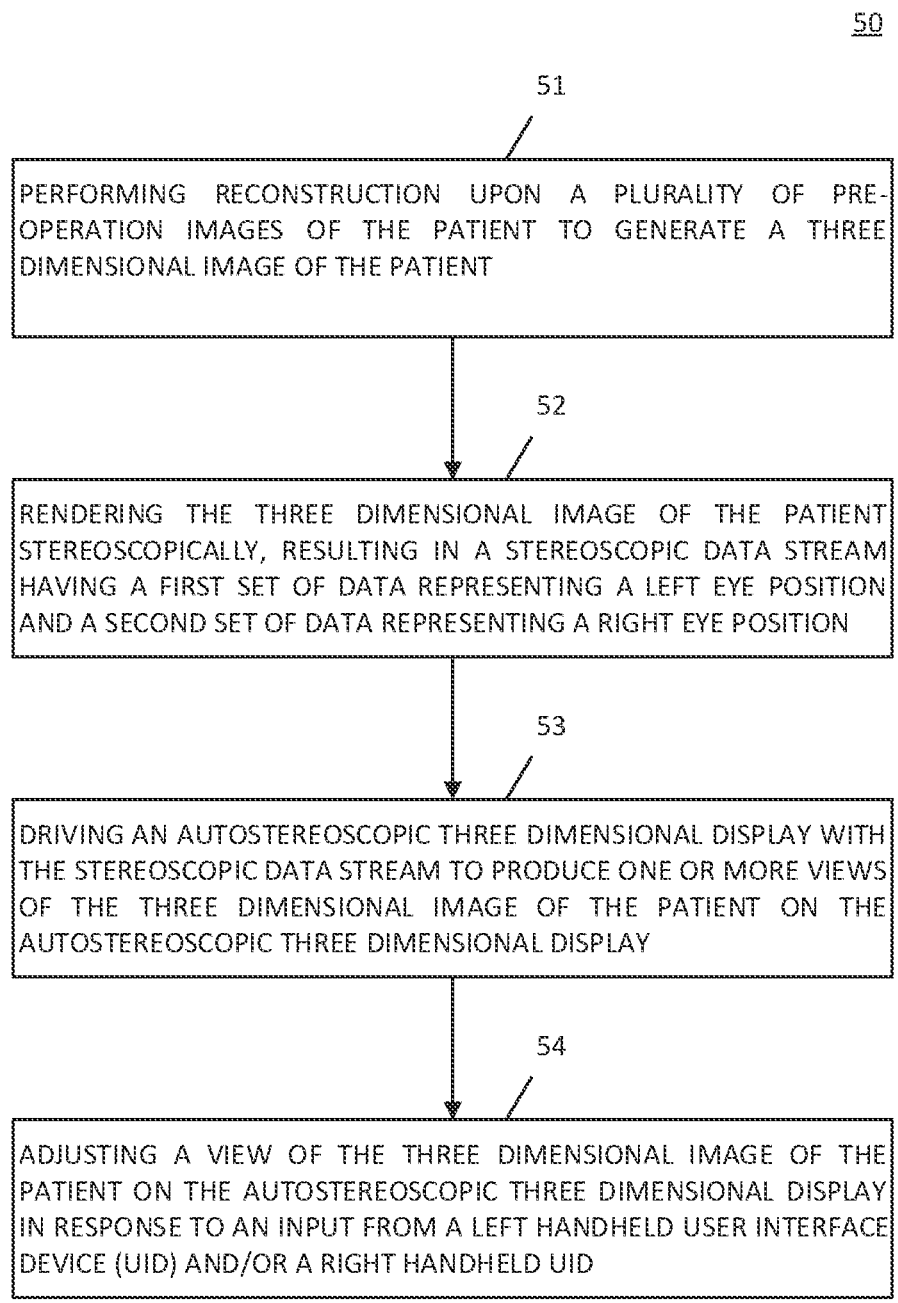
FIG. 3 shows a process for providing three dimensional viewing by a surgical robotic system, according to some embodiments.
Figure 7:
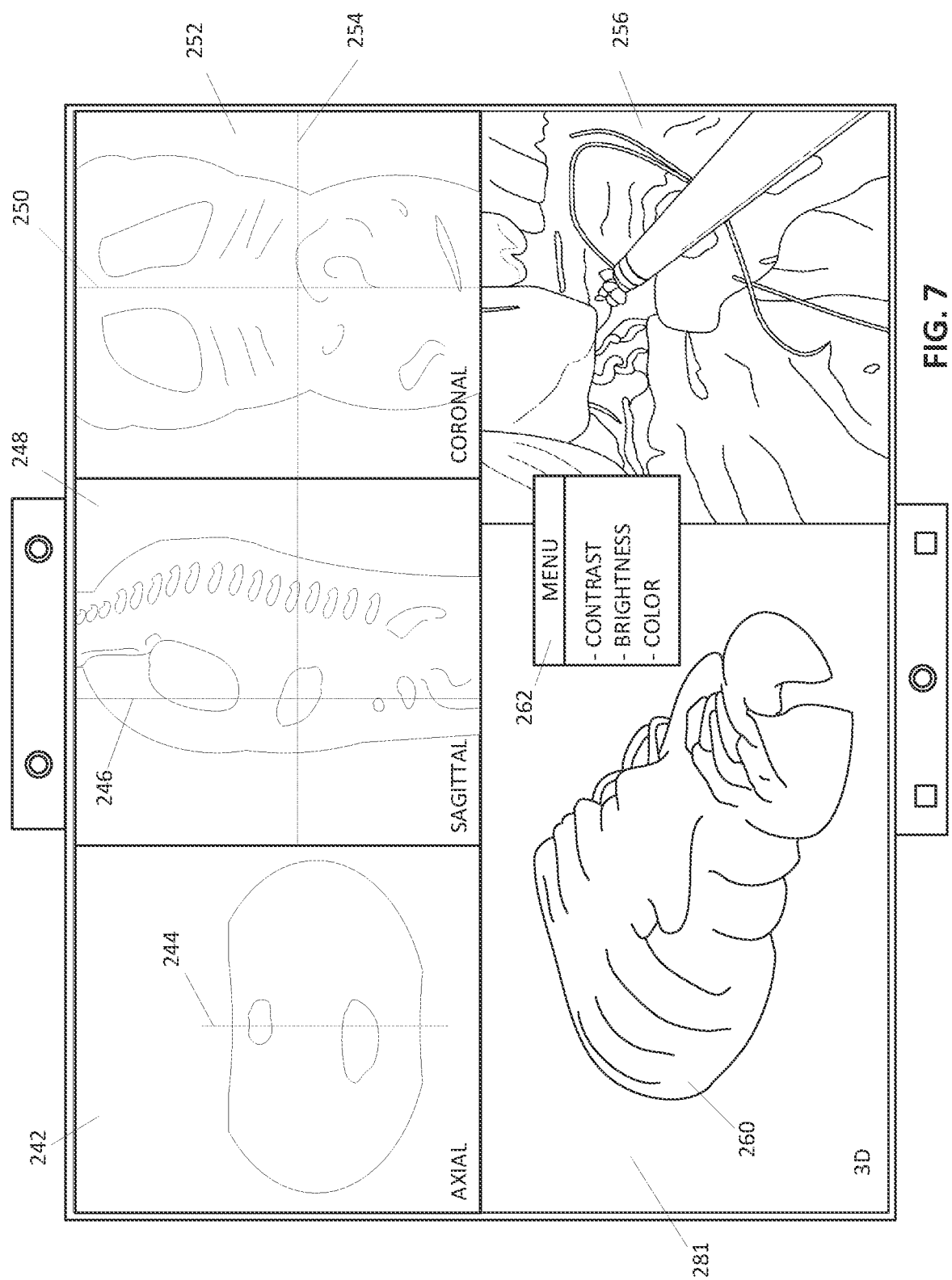

Referring to FIG. 3, a process 50 can be performed by a surgical robotic system during a surgical procedure, to help provide visual information about the patient's anatomy. One or more processors of the surgical robotic system can be configured to perform the process. At block 51, the process includes performing reconstruction upon a plurality of pre-operation images of the patient to generate a three dimensional image of the patient. MPR can also be performed to generate MPR views (e.g., an axial view, a sagittal view, and a coronal view as shown in FIG. 7).

At block 52, the process includes rendering the three dimensional image of the patient stereoscopically, resulting in a stereoscopic data stream having a) a first set of data representing visual data that a left eye would see at a left eye position, and b) a second set of data representing visual data that a right eye would see at a right eye position. As discussed, virtual cameras can be virtually located in the same scene and share a single Open GL context to capture images, virtually, of the three dimensional image, to produce the corresponding sets of data. By 'virtual camera', this means that virtual image data is generated from the point of view of a camera, simulated by a computer, in computer simulated space (virtual space).

At block 53, the process includes driving an autostereoscopic three dimensional display with the stereoscopic data stream to produce one or more views of the three dimensional image of the patient on the autostereoscopic three dimensional display. Showing images three-dimensionally to the user requires a three dimensional monitor. As described, the user console can include a surgical monitor for controlling the surgical robotic arms and attached tools. In some cases, a user can wear 3D glasses while viewing the surgical monitor to create a three dimensional effect. In some cases, an auto stereoscopic or "glasses-free" display can be deployed in the user console, to might make wearing glasses unnecessary. The process can generate a visualization pipeline that combines a) the rendered three dimensional images of the patient, and b) images coming from the endoscope to form a hybrid view having three dimensional images of the patient as well as a live feed of the patient surgery that is not three dimensional.

At block 54, the process includes adjusting a view of the three dimensional image of the patient on the autostereoscopic three dimensional display in response to an input from a left handheld user interface device (UID) and a right handheld UID. The three-dimensional display can be the same as one used to control surgical robotic arms, thereby allowing the user to seamlessly refer to a patient's anatomy in 3D while performing the surgical procedure. Similarly, the UIDs can be the same as those used to control the surgical robotic arms. A "clutch", such as a foot input device, voice recognized command, or UID input, can be used to toggle control between using the UIDs to a) control the surgical robotic arms, and b) adjust the view of the patient's anatomy on the three dimensional display.

The UIDs provide a seamless and intuitive way to interact with the image viewer application. The UIDs can be used as cursors by tracking position (location and orientation) of each UID. In some embodiments, the UIDs can have a squeezable portion (e.g., a bulb portion) where squeezing the portion creates an activation state, similar to how a computer mouse press works. Different gestures, movements, and activation sequences can provide different interactions with the user interface (showing the three dimensional image and endoscope view).

For example, a user can select the image series to be displayed on the UI based on the UID inputs. If the series comprises 2D images, the UIDs can be rolled (e.g., rotated about a center axis of the UID) to scroll through the image set. In case the series represents three dimensional image data of the patient (e.g., a series of pre-operation images/slices of the patient), one is able to change the MPR planes and thus scroll through slices by rotating the UIDs. In addition, gestures with the UIDs allow adjustment of the reconstructed three dimensional image of the patient. Zooming is similar to a touch screen gesture, squeezing both UIDs while bringing them closer together or farther away from each other. The view can be changed by squeezing both UIDs and simultaneously translating them in the same direction. Rotations can be input by squeezing and simultaneously translating just one of the UIDs. Squeezing and releasing the UIDs quickly brings up a menu where image display options like brightness and contrast can be selected. Once selected, these parameters can be modified by rotating the UID. These interactions are further described in other sections.

Figure 4:
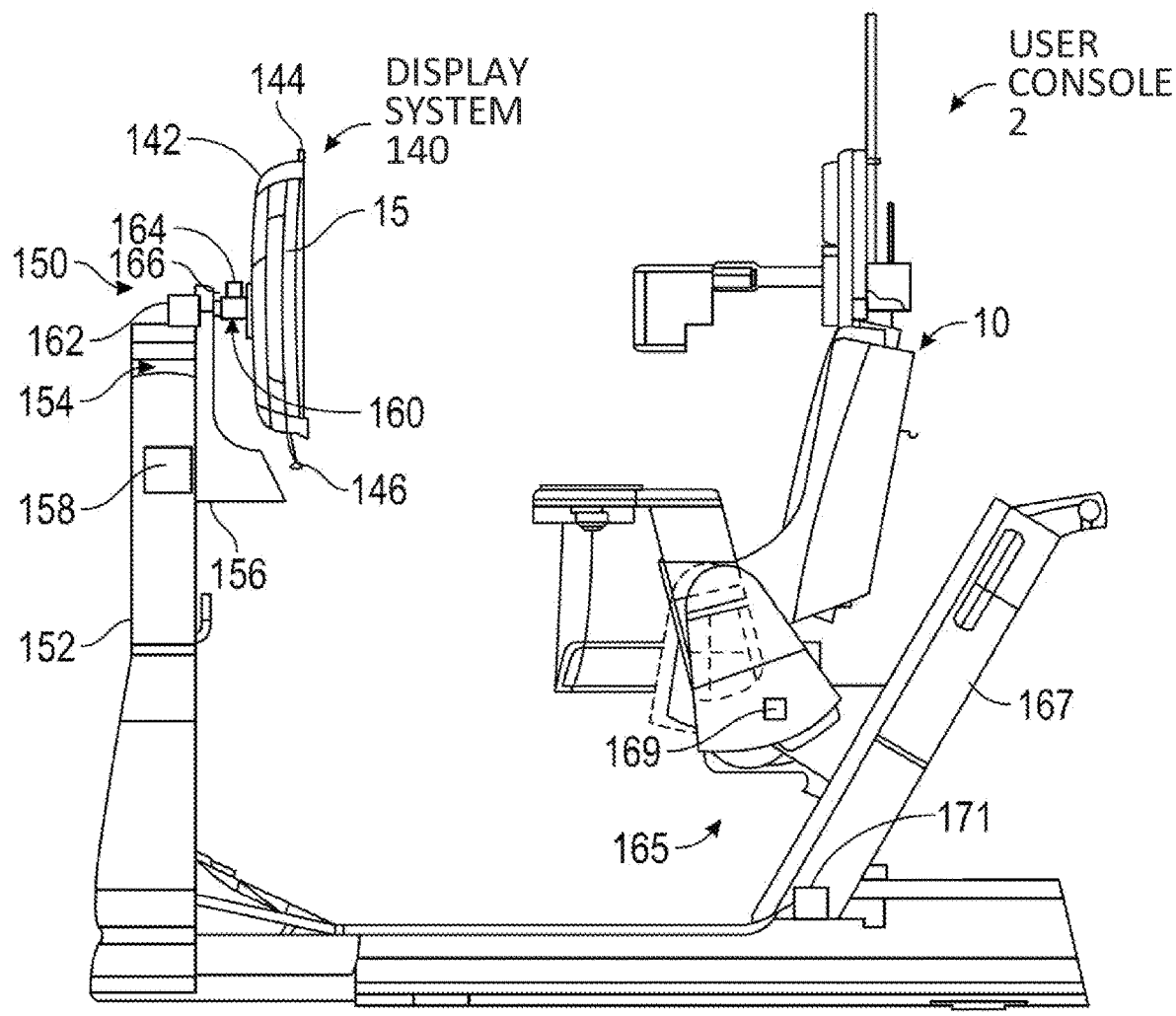
FIG. 4 shows a user console of a surgical robotic system with three dimensional viewing features, according to some embodiments.

FIG. 4 shows a schematic view of an exemplary user console 2. As shown in FIG. 2, a display system 140 can be provided for use with the user console 2 and the surgical robotic system 1. The display system 140 includes an autostereoscopic, three-dimensional display (also known as a monitor) 142 that can be driven with an autostereoscopic data stream to display three-dimensional (3D) and/or two-dimensional (2D) information to a user. The monitor 142 may display various information associated with the surgical procedure (e.g., a three dimensional image of a patient, an endoscopic camera view of the surgical site, static images, GUIs, etc.) or surgical robotic system (e.g., status, system settings), or other suitable information in the form of 2D and 3D video, image data, text, graphical interfaces, warnings, controls, indicator lights, etc. The monitor 142 as described herein further may enable the user to interact with displayed content using eye movements or other suitable gestures of the user for control of the display system and operation of other instruments such as those in the surgical robotic system.

The three dimensional display system 140 includes a plurality of sensor assemblies 144 and 146 including a first tracking sensor assembly 144 (which can include a head or eye tracking sensor), and a second tracking sensor assembly 146 (which can include a gaze tracking sensor). The first and second sensor assemblies 144 and 146 can be attached to, or in some variations integrally formed with, the monitor 142. For example, the first sensor assembly 144 can be connected to an upper or top portion of the monitor 142 and the second sensor assembly 146 can be connected to a lower or bottom portion of the monitor 142, as generally shown in FIG. 2. However, in the alternative, the second sensor assembly 146 can be attached to the top portion of the monitor 142 and the first sensor assembly 144 can be attached to the bottom portion of the monitor 142, or both the first and second sensor assemblies 144 and 146 can be attached to the top or bottom portions of the monitor 142, or the first or second sensor assemblies 144 and 146 can be attached to side portions of the monitor 142. The first or second sensor assemblies 144 and 146 also can be coupled to or incorporated with other suitable components or parts of or near the console 2, without departing from the scope of the present disclosure.

As further shown in FIG. 4, the monitor 142 may be supported by a power adjustable monitor support assembly 150. The monitor 142 may be positioned proximate or near the seat 10 to enable a user to view the monitor while the user is seated in or otherwise engaged by the seat 10. For example, the support assembly 150 may have a support or column 152 positioned in front or forward of the seat 10, which support or column 152 at least partially supports the monitor 142. In one variation, the monitor 142 is connected to the support 152 by an adjustable mount assembly 154 including an actuator subsystem with one or more actuators 158, 162, 166 that enable automatic adjustment of a position or orientation of the monitor 152 (e.g., based upon output data received from the first or second sensor assemblies 144 or 146). The monitor 142 further can include one or more sensors (e.g., position sensors, motion sensors, accelerometers, etc.) attached to the monitor 142 that facilitate the detection and tracking of positions or orientations of the monitor.

The mount assembly 154 can enable translation or rotational movement of the monitor 142 for up to six degrees of freedom including, e.g., tilt, yaw, rotation, front-to-back movement, side-to-side movement, and up-and-down movement. For example, the mount assembly 154 can include a slideable support portion or member 156 coupled to the monitor 142. The slideable support portion 156 further can be driven by one or more actuators 158 (e.g., motors, hydraulic actuators, pneumatic actuators, etc.) for up-down and side-to-side translation of the monitor 142. The mounting assembly 154 further can include one or more telescoping portions or sections 160 or other suitable portions or components that are driven by one or more actuators 162 to enable forward and backward movement of the monitor 142 (i.e., movement of the monitor 142 towards and away from the seat 10, e.g., to vary a distance between the seat 10 and the monitor 142). The telescoping portions 160 can connect the monitor 142 to the slideable support portion 156. The mounting assembly 154 also can include a pivotable connection 164 (e.g., a swivel fixture, ball joint, pivoting feature, etc.) connecting the monitor 142 to the telescoping portions 160. Movement of the monitor 142 about the pivotable connection 164 can be driven by an actuator 166 (e.g., motors, hydraulic actuators, pneumatic actuators, etc.) to enable tilt, yaw, and rotation of the monitor 142. The mounting assembly 154 further can allow for manual adjustment of the position or orientation of the monitor 142.

The seat 10 can be supported by a power adjustable seat support assembly 165. The power adjustable seat support assembly 165 can have an actuator subsystem including actuators 169/171 that drive movement of the seat 10. The seat support assembly 165 includes seat support 167 having a single pillar at least partially supporting the seat 10, but in other examples, the seat support 167 may comprise two or more pillars. The seat support 167 can be angled posteriorly in relation to the monitor 142, but in other variations, may be angled vertically straight upward or tilted anteriorly. In some variations, the seat 10 can be moveably or adjustably mounted to the seat support 167. For example, the seat 10 can rotate, tilt, recline, etc. in relation to the support 167 to enable adjustment of a position or orientation of the seat 10 in relation to the monitor 142 (e.g., such that a position of the user's head or eyes can be automatically adjusted in relation to the monitor 142 to optimize visualization or perception of three-dimensional images thereon). The seat assembly 165 further can have one or more actuators 169 (e.g., motors, hydraulic actuators, pneumatic actuators, etc.) for automatically driving rotation, tilting, reclining, etc. of the seat 10 (e.g., in response to output data from the first or second sensor assemblies 144/146).

In some variations, the seat 10 further is moveable along the support 167 (e.g., to move the seat 10 up and down and forward and backward in relation to the monitor 142). For example, an actuator 171 (e.g., a motor, a hydraulic actuator, a pneumatic actuator, etc.) can drive movement of the seat 10 along the support 167 (e.g., in response to output data from the first or second sensor assemblies 144/146). In addition, or in the alternative, the seat support 167 may be configured to change its angle or orientation, or to translate in the forward or rearward directions or in the lateral directions. In some further variations, the seat support 167 may be configured to telescope or otherwise extend or retract longitudinally or generally vertically. The seat support assembly 165 further may allow for manual adjustment the position or orientation of the seat 10.

Figure 5:
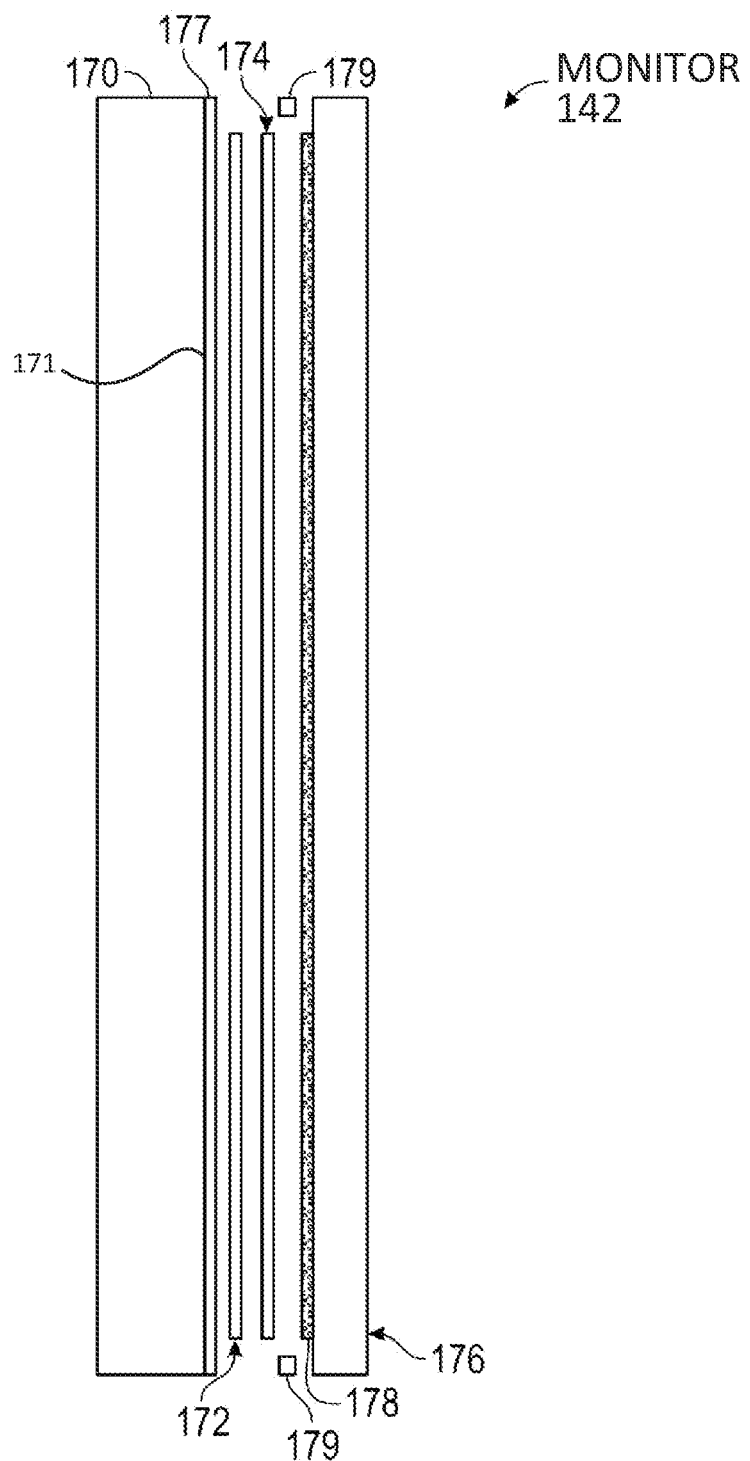
FIG. 5 shows an exploded side view of an exemplary display or monitor, according to some embodiments.

FIG. 5 shows a cross-sectional view of the display or monitor 142. The display or monitor 142 can include a flat, curved, or otherwise shaped panel display 170, such as an LCD, LED, plasma, or other suitable panel display, having a plurality of pixels for displaying two or three-dimensional images. The display 142 further can include one or more layers 172/174 at least partially overlaying, or otherwise disposed/positioned over, the display 142. The layers 172/174 are arranged on a display surface 171 of the display panel to facilitate a user's visualization of three-dimensional images on the display 142. In one embodiment, the layers 172/174 can include micro-lenses that can be at least partially positioned over the plurality of pixels of the panel display 170 to facilitate or otherwise allow for the user's visualization or perception of three-dimensional images on the panel display 170. In one embodiment, the pixels of the panel display 170 can display a left eye image and a right eye image that are continuously and/or dynamically interleaved, and the layers 172 or 174 can enable the user to visualize or perceive the left eye image and the right eye image as a single three-dimensional image, without the use of three-dimensional glasses or other additional wearable or similar components on the user. In the alternative, the one or more layers 172/174 can include polarizing filters, a patterned retarder, or dynamic shutters, and a user may use three-dimensional glasses or other similar wearable components to view or visualize three-dimensional images on the display.

The display 142 further can include a protective layer 176 at least partially covering or sealing off the layer(s) 172/174 or the panel display 170. The protective layer 176 may seal off and protect the layers 172/174 and panel display 170 such that the monitor 142 is suitable for use in a surgical environment. For example, the protective layer 176 may allow for sterilization or cleaning of the display (e.g., with cleaning chemicals, such as alcohol-based or chlorine-based cleaners) without damage to the micro-lenses 172/174. In one embodiment, the protective layer 176 can include surgical-grade glass or other surgical-grade materials (e.g., surgical-grade plastics or other suitable composite materials). The protective layer 176 further can have a thickness in the range of approximately 1 mm to approximately 3.0 mm, such as approximately 2.0 mm or other suitable integer and non-integer numbers within the range. Thicknesses of less than 1.5 mm or greater than 3.0 mm can be employed, however, without departing from the scope of the present disclosure. Additionally, or in the alternative, at least one additional protective layer 177 can be provided on the panel display 170 (e.g., between the panel display 170 and the layer(s) 170). The additional protective layer 177 can have a thickness of up to 1.0 mm, such as approximately 0.3 mm, and can be formed from plastic, glass, or other suitable material.

The protective layer 176 can be bonded to one or both of the layers 172/174 or the panel display 170 using an adhesive 178 (e.g., an optically clear adhesive or other suitable adhesive or glue). One or more spacers 179 further may be provided between the protective layer 176 and the layers 172/174 or the panel display 170. The spacers 179 can be positioned along a boundary of the protective layer 176 at equally spaced intervals, though in some variations the spacers 179 can be disposed intermittently or sporadically about the protective layer 176. The spacers 179 can prevent damage to the layers 174/176 during formation of the monitor, e.g., during application and bonding of the protective layer 176.

In some variations, as shown in FIG. 5, the first sensor assembly 144 can include one or more sensors 200. The sensors 200 can include a stereo camera(s), an infrared camera(s), or other suitable camera(s) 202 that does not filter infrared light. In one embodiment, the camera(s) 202 can include one IntelR Real Sense Camera as provided by Intel Corp. of Santa Clara, CA. The sensors 200 additionally or alternatively can include other types of cameras, e.g., color cameras, or other suitable sensing devices, without departing from the scope of the present disclosure. Signals or output information from the first sensor assembly 144 can be received and processed, e.g., by a controller or processor in communication with the first sensor assembly 144, to facilitate or otherwise allow for detection and tracking of a head or eye position of a user. For example, the first sensor assembly 144 can be used for detecting and tracking an xyz position of a user's head, eye, or eyes, e.g., in relation to an origin or an original position, such that a position, e.g., a distance, of the user's head or eyes can be continuously determined in relation to the monitor 142.

In addition, in some variations, the second sensor assembly 146 includes one or more sensors 210, such as one or more cameras 212, and one or more strobes or strobe lights 214, e.g., that flash light to facilitate detection and tracking of a gaze of a user by the camera(s) 212. The gaze of the user is detected based on a position or a movement of at least one iris of the user's eyes and includes an area or point at which the user is looking or substantially focused (e.g., an area or point on the monitor or an area or point off/away from the monitor). In one embodiment, the strobe(s) 214 can be configured to provide multiple flashes of light per second, e.g., flashes of light at a frequency in the range of approximately 80 Hz to approximately 100 Hz, such as approximately 90 Hz or other suitable frequency. The camera 212 includes a high-speed camera that is configured to capture the illuminated (e.g., by the strobes 214) and unilluminated irises of the user (e.g., such that the processor receiving and processing output data from the camera 212 can detect and track a user's irises to determine a point or area at which the user is looking or substantially focused on). The light flashes from the strobes 214 further may assist in perception of the user's eye or head position with the first sensor assembly 144, e.g., during low light conditions.

It should be understood that although some specific examples of sensor types, sensor locations, and sensor functions in the display system have been discussed above, a wide variety of other sensors and sensor types may additionally or alternatively be located throughout the various components of the display system in order to capture information about the user or for receiving user input as interactive user controls.

Figure 6:
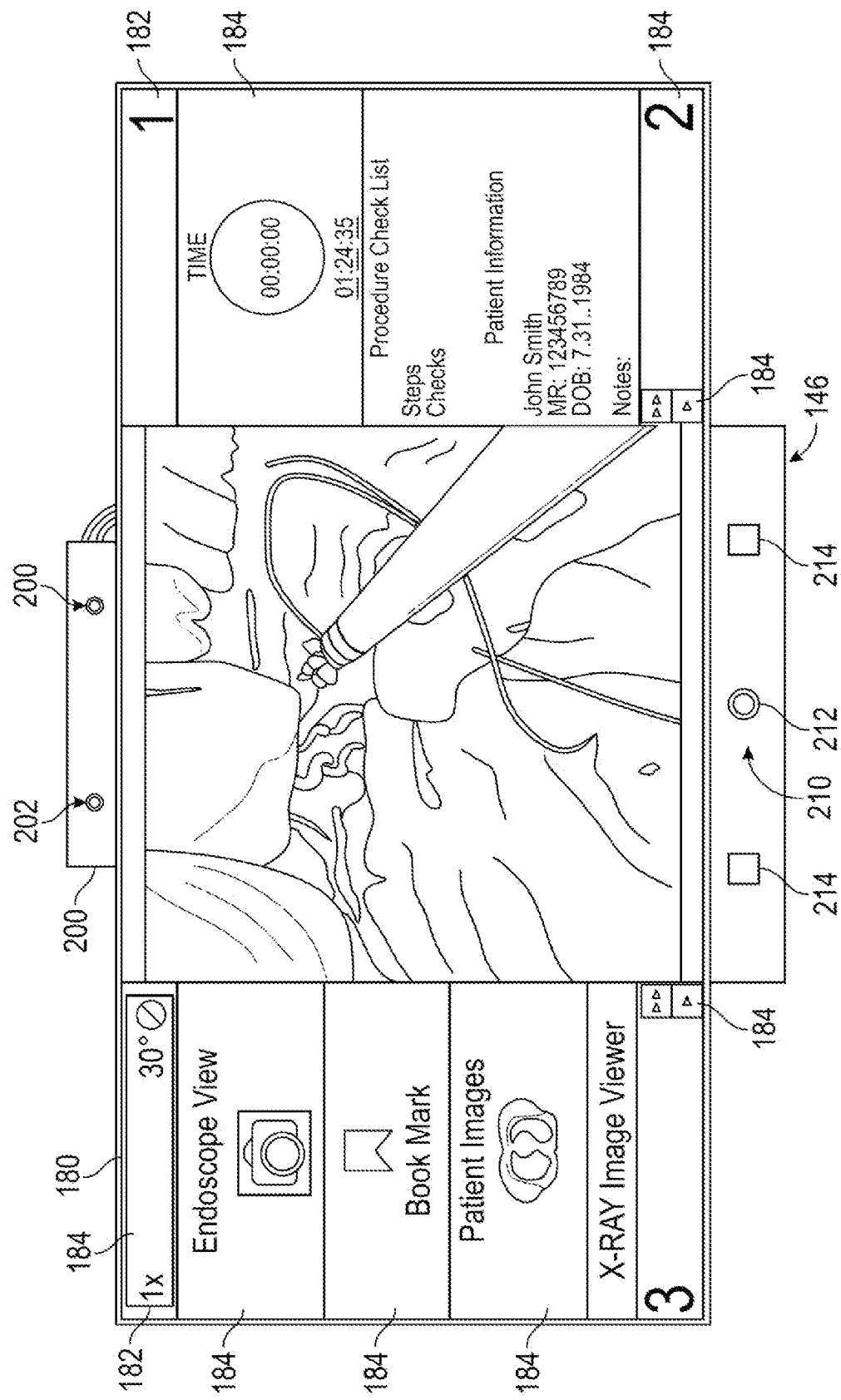
FIG. 6 and FIG. 7 show an exemplary display system for use with the surgical robotics system, according to some embodiments.

An example of a graphical user interface (GUI) to be displayed on the monitor 142 is shown in FIG. 6. For example, the GUI may display a display portion or display window 180 showing endoscopic image or other suitable surgical image data (e.g., from an endoscopic camera or other suitable surgical robotics camera placed inside the patient). The GUI may further include control panels or side panels 182 including one or more images or icons 184 related to one or more applications related to the surgical robotic system 1 (e.g., a timer application, an x-ray imaging tool, etc.). The control panel(s) 182 also can include other suitable information, such as one or more medical images (e.g., pre-operative images of patient tissue), patient data (e.g., name, medical record number, date of birth, various suitable notes, etc.), tool information (e.g., a left or right tool number, a left or right tool name, a left or right tool function, etc.). Other suitable GUIs or other display content may appear on the monitor without departing from the present disclosure. Various user interactions (e.g., the user's gaze or eye or head movements) also may cause changes to the displayed content type, as well as interaction with the applications as further described below.

The display system 140 generally includes or is in communication with a processor or controller configured to detect and track a head position or an eye position of a user relative to the monitor 142 based on processing output data of the first sensor assembly 144. In some variations, a spatial relationship between the monitor 142 and a user (e.g., a user sitting in seat 10) can be adjusted based on the detected eye or head position of the user, e.g., to optimize the user's visualization or perception of three-dimensional image data from the endoscopic or surgical robotics camera on the monitor 142. A user's perception of three-dimensional images on the monitor 142 may be optimal when the user's eyes are substantially centered with respect to the monitor 142 and spaced at a prescribed distance therefrom (e.g., approximately 70 cm to approximately 90 cm, such as approximately 80 cm from the monitor). Thus, the position or orientation of the seat 10 or the monitor 142 can be automatically (e.g., without requiring a deliberate user input) adjusted or changed to ensure that the user's head or eyes are located and positioned at an optimal orientation or viewing distance in relation to the monitor.

In one embodiment, the processor or controller can be in communication with the seat actuators 169 and 171 or the monitor actuators 158, 162, 166 and can automatically provide signals or information to seat actuators 169/171 or monitor 158, 162, 166 to adjust a position or orientation of the seat 10 or monitor 142 based upon processing output signals from the first or second sensor assemblies 144/166. For example, the processor or controller can determine a position of the user's head (or eyes) in relation to the monitor 142, and the processor can automatically generate and send a signal(s) to the seat actuators 169 or 171 or the monitor actuators 158, 162, or 166 to adjust or change the position or orientation of the seat or monitor (e.g., the seat can be reclined, tilted, rotated, moved up or down, moved side to side, etc. or the monitor can be tilted, yawed, rotated, moved front-to-back, moved side-to-side movement, moved up-and-down, etc.) based on the determined position of the user's head (or eyes), e.g., to optimize the user's visualization of three-dimensional images from the surgical robotics camera on the monitor. For example, the position or orientation of the seat or monitor can be adjusted such that the user's head (or eyes) is substantially centered with respect to the monitor and is at a prescribed distance from the monitor for optimal viewing of three-dimensional images.

The processor or controller additionally, or alternatively, can generate and send signals to the monitor 142 to display instructions thereon for manual adjustment of the monitor 142 or the seat 10 to optimize the user's perception or visualization of three dimensional image data on the display.

Furthermore, the controller or processor is configured to detect the track the gaze of the user based on processing output data of the second sensor assembly 146, and in some variations, operations of the display system 140 or the surgical robotic system 1 can be modified or controlled based on the detected gaze of the user (e.g., to facilitate control of the display system with the user's eyes or eye gestures or to stop or pause operations of the display system or surgical robotic system when the detected gaze of the user is directed away from the monitor).

In some variations, the processor or controller can be in communication with the surgical robotic system 1, and when the processor or controller determines that the gaze of a user is not directed at the monitor 142 (e.g., for a predetermined time period, such as approximately 3 seconds or up to approximately 5 seconds or more), the processor or controller is operable to automatically send a signal(s) or other output data to the surgical robotic system 1 or the display system 140 to activate or disable one or more operations thereof (e.g., to disable or freeze operation of one or more subsystems of the surgical system, such as the robotic arms 4 or the surgical tools 7, or to generate an alarm with the display system).

In one embodiment, when the processor or controller determined that the user's gaze is not directed at the monitor 142, e.g., for a prescribed time period, such as when the user is distracted, falls asleep, etc., the processor or controller automatically generates and sends one or more signals to the surgical system 1 to freeze or pause operation of the robotic arms 4 or the surgical tools 7, e.g., to prevent injury to a patient being operated on. Further, when the processor or controller determines that the user's gaze has returned to the monitor 142, the processor or controller may automatically generate and send one or more signals to the surgical system to resume operation of the robotic arms 4 or the surgical tools 7. However, the processor or controller may require a specific user input (e.g., selection of an icon, a gesture, etc.) prior to sending the signal(s) for resuming operation of the robotic arms or surgical tools 7.

Additionally, or in the alternative, when the processor or controller determines that the user's gaze is not directed at the monitor 142, the processor or controller may generate and send a signal(s) to the display system 140 to activate one or more alarms or notifications to get the attention of the user or other suitable entity (e.g., a speaker of the display system may play one or more audio sounds, the monitor may display one or more images indicating that the user's gaze is not directed at the monitor, or one or more vibrations or haptics of the seat or UIDs may be activated).

In some variations, the detected and tracked gaze of the user also can be used to initiate or control the applications on the control/side panels 182. For example, a user can look at or focus on the one or more images 184 on the control or side panels 182 to trigger application interactions. The user can initiate or close the applications, open the applications in one or more new windows or pop-up windows, control features or operations of the applications, etc. by focusing on or looking at one or more areas or points on the GUI or using other suitable eye motions. In one example, the user can focus on or look at an image associated with a timer application shown on the control/side panels, e.g., to start and stop the timer. In another example, the user can focus on or look at an image associated with an x-ray imaging tool to initiate the x-ray imaging tool (e.g., to open the x-ray imaging tool on one or more secondary or popup windows on the display). The user's gaze further can be used to close the x-ray image tool (e.g., when the user looks away or focuses on a close icon or image or other suitable feature).

Additionally, a position or orientation of the surgical robotics camera also can be updated or adjusted based on the detected and tracked gaze of the user. In some variations, the position or orientation of the surgical robotics camera can be continuously or dynamically updated (e.g., the controller or processor can automatically generate and send signals to an actuator subsystem of the surgical robotics camera to tilt, rotate, or otherwise translate a lens of the surgical robotics camera) such that an area or point on the monitor 142 that is being focused on by the user is substantially centered along the monitor 142 (e.g., centered in relation to the horizontal axis and the vertical axis of the monitor) where perception or visualization of three-dimensional image data is optimal. That is, each time a user focuses on an area or point of the three-dimensional image data displayed in the display window 180 that is not substantially centered along the display window 180 (e.g., based on the user's detected gaze), the position or orientation of the surgical robotics camera can be updated or changed such that the area or point of the three-dimensional image data on which the user is focused is moved or otherwise adjusted along the display window 180 so as to be substantially centered on the display window.

For example, the user may initially focus on a point or area of the three-dimensional image data that is substantially centered within the display window 180, and when the user changes their focus or otherwise redirects their gaze to a new area or point on the image data shown in the display window 180 (e.g., the user looks at or focuses on an area or point that is proximate to or near an edge or corner of the display window 180 or the user looks at or focuses on an area or point that is otherwise spaced apart from the original point or area in the center of the display window), the processor or controller may generate and send one or more signals to the surgical robotics camera (or a controller thereof) to automatically adjust the position or orientation of the surgical robotics camera such that the new area or point of the three-dimensional image data that is focused on by the user is moved or adjusted so as to be substantially centered within the display window 180. In this way, the position or orientation of the surgical robotics camera can be continuously or dynamically adjusted or otherwise updated based upon the determined gaze of the user such that the user's focus is directed to be and remains generally centered along the display window to facilitate optimal three-dimensional perception or visualization of the three-dimensional image data displayed therein.

During surgery, a user may navigate to a view, as shown in FIG. 7, that shows a three-dimensional image of the patient that is reconstructed based on pre-operation images. This navigation can be done through selecting a menu item on the GUI (e.g., "patient images" on FIG. 6) with input from gaze tracking, UIDs, other inputs (e.g., foot controls), or other known means (e.g., voice recognition commands).

In FIG. 7, the image viewer can show, on the three dimensional display, all studies and their series that are associated with the current surgical procedure and patient. While the image viewer is shown, an endoscope view 256 is still visible in a small window on the side of the screen. A series can be selected for viewing using the UIDs. In case the series contains only 2D images, these can be displayed taking up as much of the screen space that is available to the application as possible. The user can then use the UIDs to scroll through the images, for example by rotating them.

For series that comprise reconstructed data like CT or MRI, an MPR view and a 3D rendering is shown. The MPR view can include a sagittal view 248, a coronal view 252, and a transversal (also known as axial) view 242. Through interaction with the UIDs users can scroll through slices and define those slices to act as clip planes in the 3D view. Movement in each plane can be described as scrolling through slices of the three dimensional model of the patient. In some embodiments, inputs from the UIDs can be used to select a plane (e.g., axial, sagittal, or coronal) with respect to the three dimensional image and scrolling through cross-sectional slices of the three dimensional image of the patient, the cross-sectional slices being parallel to the selected plane.

For example, the user can use the UIDs generate inputs to move a plane 244, which would affect a change in the sagittal view; or move a plane 246, which would affect a change in the coronal view; or move plane 254, which would affect a change in the axial view.

Figure 8:
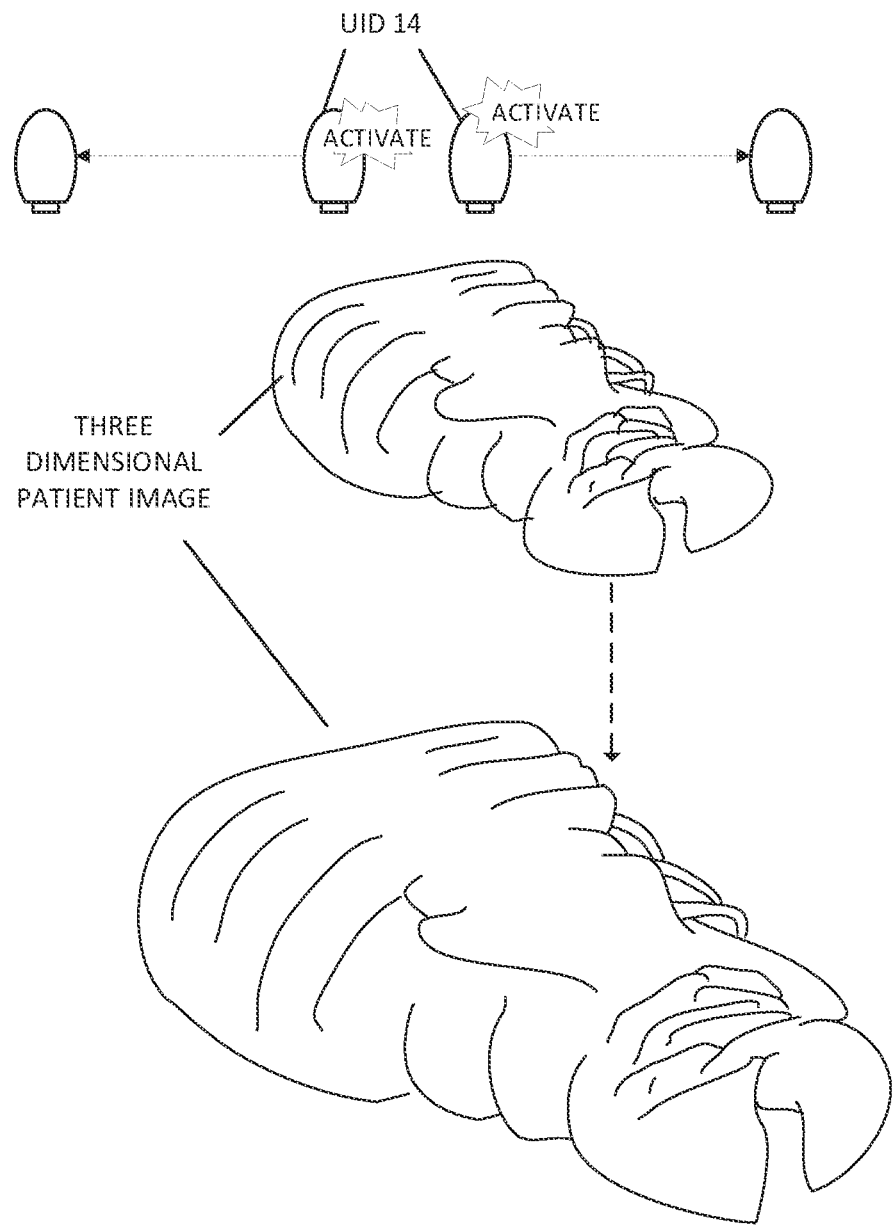
FIG. 8 and FIG. 9 illustrate examples of interacting with a three dimensional image of a patient using the surgical robotic system, according to some embodiments.

A three dimensional image of the patient 250 is also rendered on the display screen. The user can use the UIDs to "zoom in", "zoom out", rotate, and move about (translocate) the reconstructed three dimensional image. For example, referring to FIG. 8, the system can "zoom in" by increasing the size of the three dimensional image of the patient on the autostereoscopic three dimensional display in response to a user simultaneously activating and increasing the distance between the left and right UIDs 14. Conversely, to "zoom out", the system can decrease the size of the three dimensional image of the patient on the autostereoscopic three dimensional display in response to a simultaneous activation and decrease of distance between the left and right UIDs. The amount that the size is increased or decreased can be proportional to the amount of distance that is increased or decreased while both UIDs are activated. Thus, in the case of squeeze actuated bulb UIDs, a user can squeeze and bring apart the UIDs to zoom in, and squeeze and bring together the UIDs to zoom out.

Figure 9:
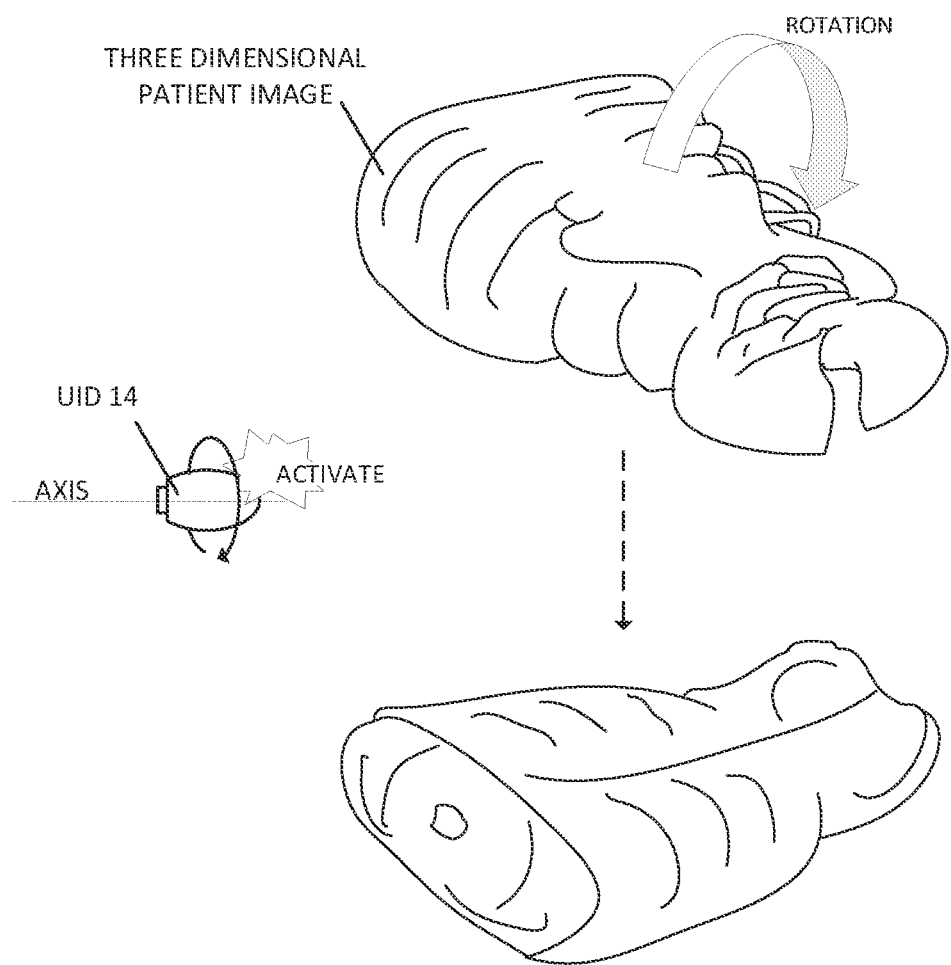

In some embodiments, the three dimensional image of the patient can be translocated (moved about in three-dimensional space) in response to a simultaneous actuation and translocation of both the left and right UIDs in the same direction. For example, if a user holds both UIDs away from the body, squeezes and brings both UIDs closer to the user's body, then this can pull the three-dimensional image of the patient towards the user. If a user holds both UIDs close to the user's body, then squeezes and brings both UIDs away from the user's body, then this can push the three-dimensional image of the patient away from user. Other coordinated movements of the user with the UID can move the three dimensional images up, down, left, right, etc. In some embodiments, as shown in FIG. 9, the system can rotate the three dimensional image of the patient on the autostereoscopic three dimensional display in response to a simultaneous activation and rotation of a single UID 14. The UID can be rotated about a longitudinal axis of the UID.

As mentioned, the system can track activation states of the UIDs. Further, the locations and orientations of the UIDs are tracked. The UIDs can have trackers built in to each UID (inside-out tracking), or trackers located external to the UIDs (outside-in tracking) that track the positions (including position and orientation) and movement of the UIDs. In the case of inside-out tracking, each UID can have a camera (e.g., infrared) housed on or within the UID. In some cases, although not required, infrared markers can be placed in stationary locations (e.g., fixed on or around the user console) and tracked by the camera. Other visual odometry techniques can be used to determine location, position, and movement of the UIDs based on images captured from cameras of the UIDs.

In FIG. 7, a selectable menu 262 can be rendered on the autostereoscopic three dimensional display in response to UID inputs. For example, a brief activation period of one of the left or right UIDs can bring the menu up, while another brief actuation activation can call the menu away. The menu can have selectable items that adjust display preferences such as, but not limited to, contrast, brightness, and/or color. When one of the menu items is selected, these parameters can be adjusted by rotating a UID. A brief activation period can be, for example, less than one second, less than half a second, or less than a quarter second.

In some existing medical image viewing solutions, patient imaging taken for pre-operative planning is unavailable to a surgeon intra-operatively (during surgery). Even in solutions where this imaging is available intra-operatively, there are other barriers to this information being effective, such as, for example, different modality of image (e.g., CT, MRI, x-rays, ultrasound, etc.), different patient anatomy, and different views of patient anatomy that are not synchronized and/or shown on different displays. Some existing solutions do not allow for simple creation of annotations and segmentations that can be viewed intra-operatively. Existing solutions are also deficient in that they do not simultaneously show different image studies that have different modalities. Further, some solutions that do simultaneously show different images do not perform co-registration of different images (e.g., from different modalities). As such, these images are not synchronized to show a common focal point, such as an organ, tissue, an annotated segmentation, or other focal point.

Figure 10:
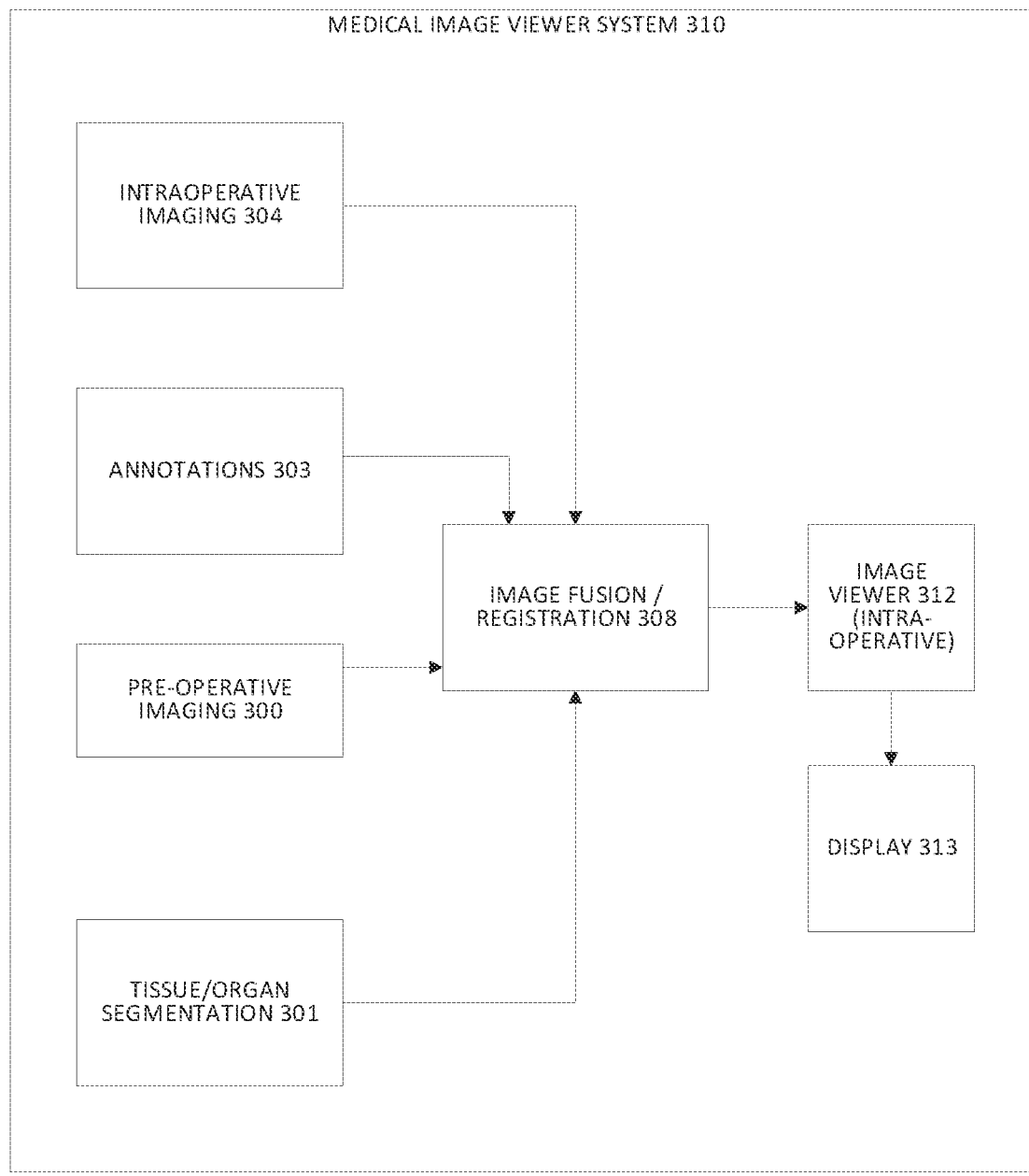
FIG. 10 shows a medical image viewer, according to some embodiments.

FIG. 10 shows a medical image viewer system 310, according to some embodiments. Such a system can be incorporated as a display in the user console of a surgical robotic system, for example, user console 2 as shown in FIG. 1. The system can include features described in the present disclosure, such as those described in relation to FIGS. 2-9.

In FIG. 10, the system 310 combines pre-operative images (e.g., CT, MRI, and other pre-operative imaging) of a patient with real-time, intra-operative imaging modalities (endoscope feed, x-ray, ultrasound), allowing for simultaneous visualization of these images. In some embodiments, the system includes fusion (e.g., registration) of multimodal images. The medical image viewer also shows annotations (e.g., surface segmentations) that can be made pre-operatively, and shown intra-operatively, thus providing improved surgical guidance.

The system 310 provides simultaneous viewing of pre-operative and intra-operative imaging in different portions of a display, and/or combined in a single view. The images (e.g., of different modalities) can be co-registered, such that direct comparison and association can be made between intra-operative and post-operative views of patient anatomy. Images of different modality can be synchronized in time and space to show a focal point of the anatomy of a patient.

At block 300, pre-operative imaging is captured of a patient. For example, a CT scanner can generate CT scans showing anatomy of a patient. Similarly, an MRI can generate MRI imagery of the patient.

At block 301, segmentation can be performed, using the captured pre-operative imagery. A medical image be represented by assigning intensities to each pixel (in 2D) or voxel (in 3D) of the image. The image can be partitioned by assigning a class to each pixel or voxel of those images, resulting in a segmentation of the image. Such segmentations can be obtained by manual annotation and/or semi-automated annotation. For 3D visualizations in particular, segmentations are useful to make structures which are currently not of interest transparent. For example, the image viewer can make anatomical structures that are present in a segmented image, but not of interest, transparent, thereby improving visibility of a focal point (e.g., an area of interest). Classifications for each pixel or voxel can include, for example, an organ type (liver, intestine, stomach, etc.), a tissue, a lesion, annotation, a tumor, etc. Thus, each pixel or voxel of an image can have a classification.

At block 303, the system can receive pre-operative annotations from a user. For example, the system can receive input from a user, and based on the input, add a marking or note to landmarks, distances, curves, and/or surfaces that are shown in the pre-operative images taken at block 300, or the segmented images resulting from block 301. The image viewer can show these annotations intra-operatively. In some embodiments, the system can also call upon saved viewpoints or perspectives intra-operatively. As such, annotations, viewpoints, and perspectives that can be made pre-operatively can be called upon for aid during a surgical procedure.

At block 304, intra-operative imaging is captured. Intra-operative imagery can include endoscope images, ultrasound, or other image capture technology. The intra-operative imagery is captured in real-time during a surgical procedure. The endoscope can be controlled manually or by a surgical robotic arm such as those described in other sections.

At block 308, one or more image registration algorithms are applied to two or more different data sets such as the pre-operative images from block 300, the segmented images from block 301, the annotated images from block 303, and/or the intra-operative imaging from 304. In some embodiments, the system applies one or more 2D-3D registration algorithms. 2D-3D registration algorithms take a 3D volume, a 2D projection view, and make an initialization or initial guess as to where to start the alignment of the 3D volume and the 2D projection. Some algorithms use trained deep learning models to initialize this optimization procedure, as well as to aid with the alignment procedure based on differing cost metric, such as normalized cross correlation or binary cross entropy losses. An example of a type of registration algorithm that can be used for 2D-3D registration is intensity-based deformable registration using a grid-based parameterization, as described in Klein, Stefan, et al. "Elastix: a toolbox for intensity-based medical image registration." IEEE transactions on medical imaging 29.1 (2009): 196-205. Such an algorithm may use B-splines or free-form deformations (FFDs) for parameterization. Other registration algorithms can also be applied.

At block 312, the image viewer renders images of anatomy of the patient in different views and in different portions of a display 313. In some embodiments, the medical image viewer includes a volumetric data renderer that displays a three-dimensional image from variable angles. In some embodiments, the medical image viewer includes a two dimensional renderer that displays x-ray or other planar images. The display can, in some embodiments, be a stereoscopic display as described in other sections. Additionally, or alternatively, the display can be integral to a tablet computer. In some embodiments, the user can generate inputs with handheld UIDs such as those used to control the surgical robotic system, to control the display, select focal points, select pre-operative annotations, make intra-operative annotations, and/or pan through 'slices' of the MPR view. Additionally, or alternatively, a user can generate the inputs via a touchscreen user interface. In some embodiments, focal points can be saved to computer readable memory and called upon later.

In some embodiments, the image viewer renders a pre-operative three-dimensional image that includes anatomy of a patient to a first section of a display. Simultaneously, an MPR view of the anatomy is rendered to a second portion of the display, and an intra-operative image of the anatomy is rendered to a third portion of the display. Based on the co-registration of the pre-operation three-dimensional images and the pre-operative images shown in the MPR view, the system can synchronize the three-dimensional image and the pre-operative image to show a common focal point of the anatomy.

For example, referring back to FIG. 7, the first portion 281 of the display can show a three-dimensional representation of the patient anatomy 260. The MPR view (242, 248, and 252) can form the second section of the display. The endoscopic view 256 forms the third portion of the display. A focal point of the patient's anatomy can be selected as, for example, an organ (liver, stomach, intestine, etc.), a tumor, or tissue. The focal point can also be any structure of the anatomy, or portion thereof, that is annotated at block 303. Registration of the images and annotations provides a mapping for different image modalities and/or annotations so that they can be synchronized when viewing a common focal point.

Figure 11:
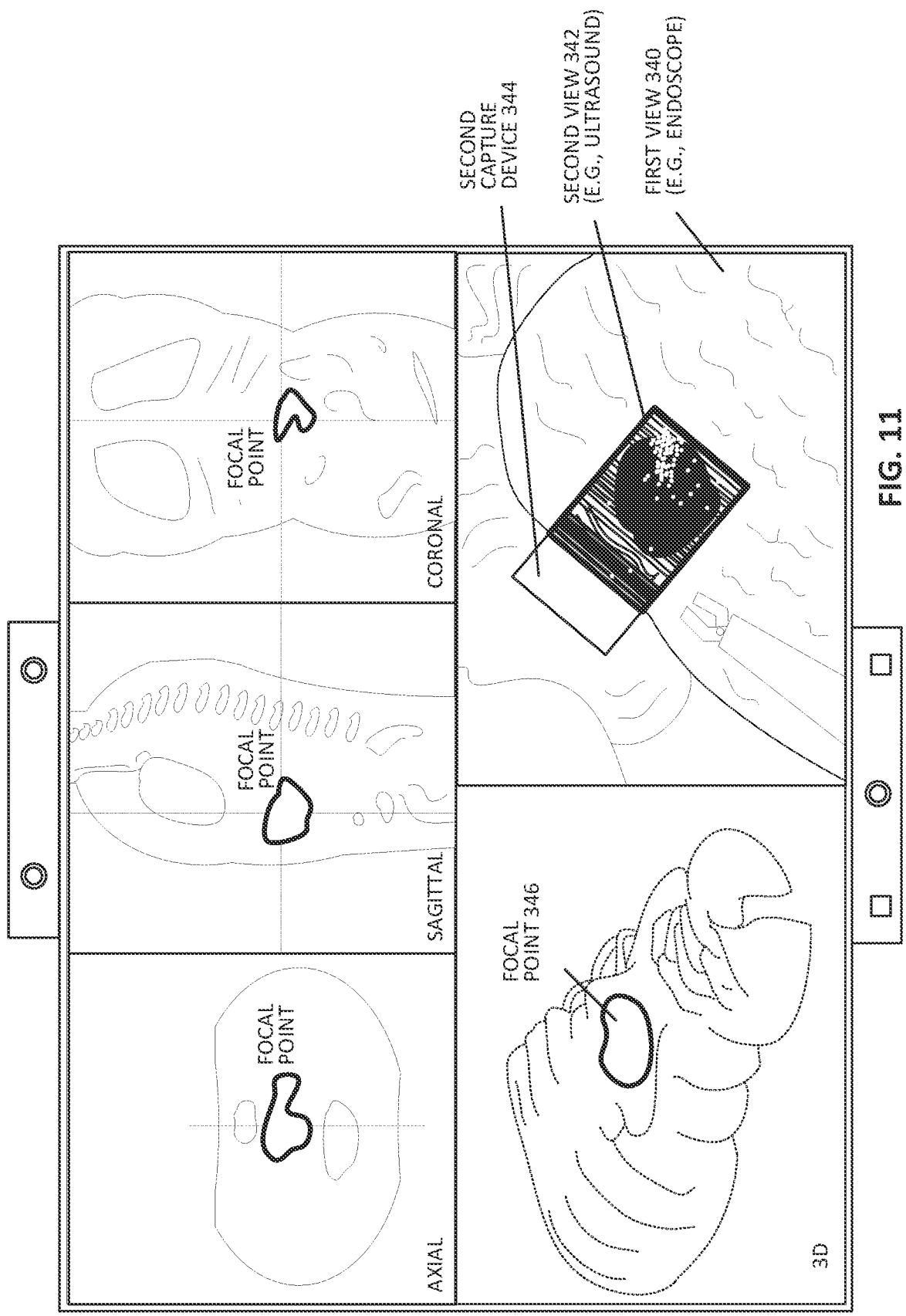
FIG. 11 shows a display system for use with surgical robotics system, according to some embodiments.

For example, as shown in FIG. 11, if the focal point 346 is a tumor, organ, annotated structure, etc., in the abdomen, then transparency of other anatomical structures (e.g., tissue, bone, muscle, organs) shown in the three-dimensional image can be increased to highlight the focal point. Alternatively, or additionally, the focal point can be highlighted by adjustment of color and/or brightness of the focal point in a manner that contrasts the focal point from the other anatomical structures. Alternatively, or additionally, the three-dimensional image can be arranged (e.g., centering the focal point or rotating the image) to emphasize the focal point. Simultaneously, the same focal point can be highlighted such as with an outline, color, brightness, or other visual indicator, in each of the MPR views. Additionally, or alternatively, the plane of each MPR view (244, 246, 254 as shown in FIG. 7) can be arranged to pass through the focal point in each MPR view. In such a manner, the anatomy as shown can be arranged or highlighted in the different portions of the display during operation. Different focal points can be selected or called upon to visualize different parts of the anatomy from different views. This can help a user navigate surgical tools through the anatomy during performance of the surgery.

The MPR view includes at least two of a sagittal view, a coronal view, or a transversal view. In some embodiments, the MPR view includes all three views. As mentioned, the MPR views can be arranged based on focal point. The focal point can be selected based on input from a user through one or more user interfaces. For example, the user can use a handheld UID as described in other sections to select the focal point. The focal point can be an item in a menu, or an active selectable portion of any of the images. In some embodiments, if the display is shown on a touchscreen, the user can provide the input through the touchscreen display.

In some embodiments, the three-dimensional view can be superimposed on and/or aligned with the intra-operative view. For example, referring to FIG. 7, the three-dimensional image of the patient anatomy 260 can be superimposed over the endoscopic view 256 to provide a three-dimensional understanding of the anatomy shown in the endoscope, and to provide additional emphasis on one or more points of interest (e.g., a focal point that is highlighted). The three-dimensional image and/or focal point can co-registered with the endoscope feed, such that the three-dimensional image is spatially synchronized with the anatomy shown in the endoscope feed.

In some embodiments, a plurality of sources of intra-operative imaging can be fused at block 308 and shown in a fused manner by the image viewer. For example, as shown in FIG. 11, a first view 340 occupies a third portion of the display that shows intra-operative images of patient anatomy that is captured by a first intra-operative capture device, e.g., an endoscope. The capture device can be located inside of the patient during surgery to help guidance of one or more surgical tools that can be manually or robotically controlled. A second intra-operative view 342 shows a second image feed that is generated with a second capture device 344 (e.g., an ultrasound scanner). The second image feed (ultrasound) can be co-registered with the first intra-operative image feed (endoscope) to create spatial mapping between the two. This can include spatial tracking of the endoscope, for example, by position sensors and/or cameras. Based on the co-registration of the two image feeds, the system can spatially map the second intra-operative view 342 to the first intra-operative view 340 (e.g., endoscope images) to fuse the second view and the first view together. In this manner, a user can see 'inside' of some anatomy (e.g., with ultrasound) that may not be visible with otherwise (e.g., using the endoscope alone).

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications, and they thereby enable others skilled in the art to best utilize the invention and various embodiments with various modifications as are suited to the particular use contemplated.

What is claimed is:

1. A surgical robotic system comprising:
   a left handheld user interface device (UID) and right handheld UID;
   an autostereoscopic three dimensional display; and
   a processor, configured to
      receive a plurality of pre-operation images of a patient;
      perform reconstruction upon the plurality of pre-operation images to generate a three dimensional image of the patient;
      render the three dimensional image of the patient stereoscopically, resulting in a stereoscopic data stream;
      drive the autostereoscopic three dimensional display with the stereoscopic data stream to produce one or more views of the three dimensional image of the patient on the autostereoscopic three dimensional display; and
      adjust a view of the three dimensional image of the patient that includes translocating the three dimensional image of the patient within the view in response to a simultaneous activation and translocation of at least one of the left handheld UID and the right handheld UID in a direction.

2. The surgical robotic system of claim 1, wherein the processor is further configured to control movement of a plurality of surgical robotic arms in response to additional input from the left handheld UID or the right handheld UID, to perform surgery upon the patient.

3. The surgical robotic system of claim 1, wherein each of UIDs has a bulb that is activated upon being squeezed and deactivated upon being released, and the processor is further configured to monitor whether the bulb is activated or deactivated.

4. The surgical robotic system of claim 1, wherein the autostereoscopic three dimensional display simultaneously produces an endoscope view based on images received from an endoscope.

5. The surgical robotic system of claim 1, wherein adjusting the view of the three dimensional image of the patient includes selecting a plane with respect to the three dimensional image and scrolling through cross-sectional slices of the three dimensional image of the patient, the cross-sectional slices being parallel to the selected plane.

6. The surgical robotic system of claim 1, wherein adjusting the view of the three dimensional image of the patient includes a) decreasing a size of the three dimensional image of the patient on the autostereoscopic three dimensional display in response to a simultaneous activation and decrease of a distance between the left handheld UID and the right handheld UID, or b) increasing the size of the three dimensional image of the patient on the autostereoscopic three dimensional display in response to a simultaneous activation and increase of the distance between the left handheld UID and the right handheld UID.

7. The surgical robotic system of claim 1, wherein adjusting the view of the three dimensional image of the patient includes rotating the three dimensional image of the patient on the autostereoscopic three dimensional display in response to a simultaneous activation and rotation of only one of the left handheld UID or the right handheld UID.

8. The surgical robotic system of claim 1, wherein the processor is further configured to render a selectable menu on the autostereoscopic three dimensional display in response a brief activation period of one of the left handheld UID or the right handheld UID.

9. The surgical robotic system of claim 1, wherein the autostereoscopic three dimensional display includes one or more layers, at least partially positioned over a display surface of the autostereoscopic three dimensional display to facilitate a user's visualization of the three dimensional image on the display surface, the one or more layers including at least one of polarizing filters, a pattern retarder, or dynamic shutters.

10. The surgical robotic system of claim 9, wherein the user is to use glasses or other wearable components to view the three dimensional image of the patient on the autostereoscopic three dimensional display.

11. The surgical robotic system of claim 1, wherein the processor is further configure to detect and track a head position of a user relative to a display surface of the autostereoscopic three dimensional display based on data received from an infrared camera; and
 modify operation of the autostereoscopic three dimensional display based on a detected gaze of the user, and
 automatically adjust a spatial relationship between the user and the display surface based on the head position of the user to affect the user's visualization of the three dimensional image on the autostereoscopic three dimensional display.

12. The surgical robotic system of claim 1, wherein
 the three dimensional image is rendered to a first portion of the autostereoscopic three dimensional display,
 a multi planar reconstruction (MPR) view is rendered to a second portion of the autostereoscopic three dimensional display,
 an intra-operative image is rendered to a third portion of the autostereoscopic three dimensional display, and
 the three dimensional image and the MPR view are synchronized to show a common focal point of anatomy of the patient.

13. A method, performed by a computing device of a surgical robotic system, comprising:
 receiving a plurality of pre-operation images of a patient;
 performing a reconstruction upon the plurality of pre-operation images to generate a three dimensional image of the patient;
 rendering the three dimensional image of the patient stereoscopically, resulting in a stereoscopic data stream;
 driving an autostereoscopic three dimensional display with the stereoscopic data stream to produce one or more views of the three dimensional image of the patient on the autostereoscopic three dimensional display; and
 adjusting a view of the three dimensional image of the patient that includes translocating the three dimensional image of the patient within the view in response to a simultaneous activation and translocation of a left handheld user interface device (UID) or a right handheld UID in a direction.

14. The method of claim 13 further comprising controlling movement of a plurality of surgical robotic arms in response to additional input from the left handheld UID or the right handheld UID, to perform surgery upon the patient.

15. The method of claim 13, wherein each of UIDs has a bulb that is activated upon being squeezed and deactivated upon being released, and the method further comprises monitoring whether the bulb is activated or deactivated.

16. The method of claim 13, wherein the autostereoscopic three dimensional display simultaneously produces an endoscope view based on images received from an endoscope.

17. The method of claim 13, wherein adjusting the view of the three dimensional image of the patient comprises selecting a plane with respect to the three dimensional image and scrolling through cross-sectional slices of the three dimensional image of the patient, the cross-sectional slices being parallel to the selected plane.

18. The method of claim 13, wherein adjusting the view of the three dimensional image of the patient comprises a) decreasing a size of the three dimensional image of the patient on the autostereoscopic three dimensional display in response to a simultaneous activation and decrease of a distance between the left handheld UID and the right handheld UID, or b) increasing the size of the three dimensional image of the patient on the autostereoscopic three dimensional display in response to a simultaneous activation and increase of the distance between the left handheld UID and the right handheld UID.

19. The method of claim 13, wherein adjusting the view of the three dimensional image of the patient comprises rotating the three dimensional image of the patient on the autostereoscopic three dimensional display in response to a simultaneous activation and rotation of only one of the left handheld UID or the right handheld UID.

20. The method of claim 13 further comprising rendering a selectable menu on the autostereoscopic three dimensional display in response a brief activation period of one of the left handheld UID or the right handheld UID.

21. The method of claim 13 further comprising:
 detecting and tracking a head position of a user relative to a display surface of the autostereoscopic three dimensional display based on data received from an infrared camera;
 modifying operation of the autostereoscopic three dimensional display based on a detected gaze of the user; and
 automatically adjusting a spatial relationship between the user and the display surface based on the head position of the user to affect the user's visualization of the three dimensional image on the autostereoscopic three dimensional display.

22. The method of claim 13, wherein
 the three dimensional image is rendered to a first portion of the autostereoscopic three dimensional display,
 a multi planar reconstruction (MPR) view is rendered to a second portion of the autostereoscopic three dimensional display,
 an intra-operative image is rendered to a third portion of the autostereoscopic three dimensional display, and
 the three dimensional image and the MPR view are synchronized to show a common focal point of anatomy of the patient.

* * * * *